(12) United States Patent
Hörnig

(10) Patent No.: US 8,292,947 B2
(45) Date of Patent: Oct. 23, 2012

(54) CATHETER FOR PRODUCING A STENT CONTAINING PLASTIC

(75) Inventor: Mathias Hörnig, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1888 days.

(21) Appl. No.: 11/441,318

(22) Filed: May 25, 2006

(65) Prior Publication Data

US 2007/0032859 A1    Feb. 8, 2007

(30) Foreign Application Priority Data

May 30, 2005  (DE) .......... 10 2005 024 626

(51) Int. Cl.
    *A61F 2/06* (2006.01)
(52) U.S. Cl. ...................................... 623/1.21
(58) Field of Classification Search ............. 623/1.11, 623/1.12, 1.15, 1.19, 1.21, 1.32; 606/192, 606/194, 195, 200
    See application file for complete search history.

(56) References Cited

U.S. PATENT DOCUMENTS

| | | | | |
|---|---|---|---|---|
| 4,545,367 | A | * | 10/1985 | Tucci .......................... 128/898 |
| 5,674,287 | A | * | 10/1997 | Slepian et al. ............... 128/898 |
| 5,899,917 | A | * | 5/1999 | Edwards et al. ............. 606/195 |
| 6,039,757 | A | * | 3/2000 | Edwards et al. ............. 623/1.21 |
| 6,063,112 | A | * | 5/2000 | Sgro .......................... 623/1.12 |
| 6,709,455 | B1 | * | 3/2004 | Chouinard ................. 623/1.32 |
| 2004/0148014 | A1 | | 7/2004 | Nuutinen et al. |
| 2004/0167600 | A1 | * | 8/2004 | LaFont et al. ............... 623/1.11 |
| 2005/0038493 | A1 | * | 2/2005 | Feeser ........................ 623/1.11 |
| 2005/0154439 | A1 | * | 7/2005 | Gunderson ................. 623/1.11 |

FOREIGN PATENT DOCUMENTS

| | | |
|---|---|---|
| DE | 692 02 308 T2 | 1/1993 |
| DE | 44 47 101 A1 | 7/1996 |
| DE | 199 51 279 A1 | 4/2000 |
| EP | 1 464 300 A1 | 10/2004 |
| WO | WO 94/24962 A1 | 11/1994 |

* cited by examiner

*Primary Examiner* — Ryan Severson
*Assistant Examiner* — David Eastwood

(57) ABSTRACT

In order to create a stent, which despite being simple to guide in the relevant body conduit allows flexible adaptability to the body conduit in a simple manner while avoiding undesirably high expansion forces on the wall of the body conduit, in accordance with the invention a catheter is provided, with an essentially tubular filling area surrounding the part of the catheter which can be introduced into the body conduit, which can be filled with a plastic mass which forms the stent by a process of hardening; there is provision for positioning the filling area at the position intended for the stent in the body conduit, for hardening the plastic mass in the filling area, for creating the stent and for removing the catheter from the body conduit with the stent remaining in the body conduit.

14 Claims, 3 Drawing Sheets

CATHETER FOR PRODUCING A STENT CONTAINING PLASTIC

CROSS REFERENCE TO RELATED APPLICATIONS

This application claims priority of German application No. 10 2005 024 626.5 filed May 30, 2005, which is incorporated by reference herein in its entirety.

FIELD OF THE INVENTION

The invention relates to a catheter for producing a stent containing plastic, with simultaneous positioning of this stent in body conduit, especially in the form of a blood vessel.

BACKGROUND OF THE INVENTION

A stent is a tubular implant which provides radial outwards support for the wall of a body conduit, e.g. a blood vessel, bile duct, an air conduit or an esophagus. The stent usually consists of the elastic material, e.g. a metal or metal alloy or a polymer and frequently has a mesh or network or spiral-type structure, with stents in the form of a metal mesh being the most widely used. The stent is introduced into the relevant body conduit with the aid of a catheter and once in place, is bought into adhesive contact with the wall of the body conduit. Stents are used in particular with blood vessels as endoluminal vessel prostheses in the vessel wall for artherosclerotic stenosis therapy.

Contracting the stent to make it easier to introduce into the body conduit, introducing it in the contracted state with the aid of a catheter into the relevant body conduit and expanding the stent there with a balloon end of the catheter or by self-expansion into an expanded diameter is known from DE 199 51 279 A. The use of the high-grade elastic nickel titanium alloy Nitinol as a stent material is additionally known from DE 199 51 279 A1.

The stent used in each case must be precisely tailored in its length and in its expansion diameter to the characteristics of the relevant body conduit, in order on the one hand to sufficiently expand this conduit or support it and on the other hand so as not to slip within the body conduit, without however exercising such high expansion forces on the wall of the relevant body conduct that the result is an undesirably great expansion of the body conduit or even an injury to it. It is also known from the previously mentioned DE 199 51 279 A1, in order to avoid expansion forces which are too high, to provide the stent body at least partly with a covering which essentially prevents the stent body expanding fully in the direction of its free diameter.

A device for producing a stent, especially one containing a polymer material, is known from DE 69202308 T2. The stent consists of a cylindrical body which, when positioned at the desired location in the body conduit, can be expanded radially so that it delimits a hollow cylindrical cavity. This cylindrical body is filled before being used in the body conduit with a material which can be hardened so that after its radial expansion the device is hardened.

SUMMARY OF THE INVENTION

The underlying object of the present invention is to create a stent, which despite being simple to guide in the relevant body conduit, allows flexible adaptability to the body conduit in a simple manner while avoiding undesirably high expansion forces on the wall of the body conduit.

This object is achieved by a catheter in accordance with the independent claim; Advantageous embodiments of the invention are the subject of the assigned subclaims.

By filling the inventive, essentially tubular filling area surrounding a part of the catheter introduced into the body conduit with a plastic mass which can be hardened into the stent it is possible to produce the stent directly at a position in the body conduit intended for the stent, in order on the one hand to avoid an elastic expansion in accordance with the previous positioning methods and in this case any undesirably high expansion forces which may occur, and on the other hand to adapt the stent in its form to the relevant structure of the body conduit, especially avoiding sharp edges which can injure the body conduit; Through this adaptation the stent is also especially safely secured against slippage within the body conduit through a close-fitting adhesive contact with the wall of the body conduit. In addition this flexible adaptability avoids the otherwise necessary stockpiling of a large number of stents which differ for example in their form, their expansion diameter and their length. The invention also makes it possible to produce and position stents in a particularly cost-effective manner.

It is useful for the plastic material used for the plastic mass to be bio-compatible, with polymers, especially elastomers such as silicon or rubber elastomers being especially suitable as a result of their elastic properties.

Through an inner chamber connected, especially via a closable opening, to the filling area for temporarily accepting the plastic mass it is possible, for simple introduction of the catheter into the body conduit, to fill the filling area with the plastic mass only once the stent has reached its intended position. To tailor the stent particularly well to the body conduit, a filling area expandable in an attachable form by filling it with the plastic mass especially temporarily accommodated in the inner chamber, is provided. Usefully the filling area is filled by a pressure exerted on the plastic mass.

In order on the one hand to securely prevent the plastic mass from escaping into the rest of the body conduit by keeping it in the filling area, and on the other hand to enable the form of the stent to be influenced, a delimiting means is provided on the catheter which restricts the filling area and at least partly defines the form of the stent. The delimitation is particularly successful with a delimiting means in the form of an envelope completely surrounding the filling area; especially by providing a method of releasing the envelope from the catheter it is possible in a simple manner to separate the catheter from the stent, with the envelope remaining in the body conduit as a component of the stent.

In an especially simple manner the delimitation means is embodied in the form of two seals delimiting the filling area at one of the two ends in each case from the rest of the body conduit; an embodiment of the seals whereby the catheter can at least partly expand and retract them or fold them in and out makes it possible on the one hand to retract the seals for an especially simple introduction of a catheter into the body conduit and only on reaching the position intended for the stent to extend them or fold them out again and on the other hand to retract the seals or fold them in to make it especially easy to release the stent from the catheter after the hardening of the plastic mass. The extension or retraction of the seals can for example be undertaken by an expansion or by a contraction of the seals.

In accordance with an advantageous embodiment of the invention a closable capsule which only extends over part of the length of the catheter is provided as a part of the inner chamber; This makes it possible in a simple manner to introduce the plastic mass in the capsule together with the catheter into the body conduit and there to fill the filling area with the especially liquefied plastic mass from the capsule.

In accordance with a further advantageous embodiment of the invention, a tube leading to an operating end of the catheter which remains outside the relevant body conduit is provided as part of the inner chamber; This makes it possible in a simple manner to fill the filling area located at the position intended the stent with the plastic mass, especially in a liquefied form, from outside through the operating end.

Advantageously a means for liquefying and/or for hardening the plastic mass is provided by a temperature variation; this makes it possible for the plastic mass, because of its particularly good malleability in the liquid state, to be adapted especially well to any characteristics of the body conduit and makes the filling area particularly easily to fill.

To enable the internal diameter of the stent be adapted, an inflatable balloon section is provided arranged within the tubular filling area; this is inflated after positioning of the filling area in accordance with the desired internal diameter, e.g. by introducing fluid into it.

In order to additionally stabilize the stent, an embodiment of the filling area is provided for accommodating a wire mesh which can be encapsulated with the plastic mass. This wire mesh is encapsulated with the plastic mass when the filling area is filled. When a self-expanding wire mesh is used it is worthwhile to force this initially into an unexpanded form with an additional removable sheath over the wire mesh and only let it expand by removing the sheath once the intended position is reached.

An embodiment of the filling area to accept markers which can be encapsulated by the plastic mass and are impermeable to x-radiation makes it possible to create a stent of which the position and/or the sizes can be detected on an x-ray image of the relevant body conduit on the basis of the markers encapsulated into the stent; Such markers are for example rings made of gold arranged on the end of the stent.

As an alternative or in addition to the markers encapsulated into the stent, the position and/or size of the stent can be made visible by an image created by an imaging method especially on an x-ray image, by the plastic mass being mixed with either a positive or a negative contrast means. Since the mixing covers the entire stent, this stent, by contrast with the stent known from DE 199 51 279 A1 with a simple coating, can be more easily seen on the relevant image.

For an imaging process based on x-radiation for example, substances containing iodine and substances containing iron ox-ide particles for an imaging system based on magnetic resonance are suitable as a positive contrast means. The positive con-trast means can be mixed into the plastic mass especially sim-ply in powder or crystalline form, e.g. as a salt of triiodo-benzoic acid.

For an imaging method based on x-radiation and for sonography, gases such as carbon dioxide are suitable as negative contrast means for example. These gases can be mixed especially simply with the plastic mass in the form of gas bubbles encapsulated in plastic. In a practical application this mixing can be undertaken by foaming the gas through the plastic mass or by adding small plastic balls which each have the gas inside them in a hollow cavity.

To expand the body conduit to a desired diameter it is useful, before positioning the stent, to perform a balloon dilatation of the body conduit.

BRIEF DESCRIPTION OF THE DRAWINGS

The invention, as well as further advantageous embodiments of the invention in accordance with features of the subclaims, are explained in greater detail below with reference to schematic diagrams of exemplary embodiments in the drawing, without this restricting the invention to this exemplary embodiment in any way; The Figures show:

FIGS. 1-4 illustrate the inventive method for producing a stent with reference to an exemplary embodiment of an inventive catheter.

DETAILED DESCRIPTION OF THE INVENTION

Figure 1:
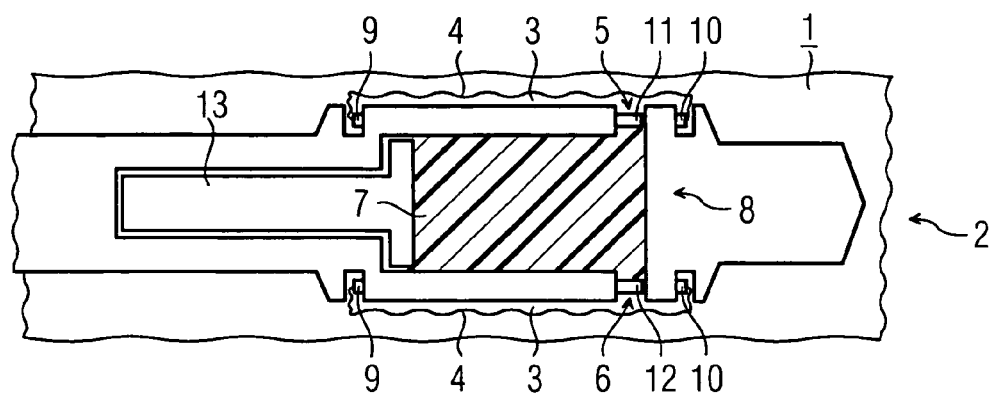
FIG. 1 a longitudinal cross section of a catheter introduced into a body conduit with a filling area which is enclosed by an envelope and which can be filled with a plastic mass, which is held in a capsule arranged in the catheter.

FIG. 1 shows, in a longitudinal section, a part of a catheter 2 introduced into a body conduit 1, with the catheter 2 being surrounded by an essentially tubular-shaped filling area 3 which is enclosed within an envelope 4 and which is connected via two openings 5 or 6 to an inner chamber, in this exemplary embodiment in the form of a cylindrical capsule 8, arranged in the catheter 2, containing a liquefied and hardenable plastic mass 7. The plastic mass 7 is mixed with a substance impermeable to x-radiation, e.g. a crystalline salt of triiodobenzoic acid. The envelope 4 is held onto the catheter 2 at its front and rear end by a clamping ring 9 or 10 which can be expanded and retracted, which encloses the entire circumference of the catheter 2 in each case, so that the filling area 3 is completely sealed from the body conduit 1. The two openings 5 and 6 each have an opening slider 11 or 12, with which the openings 5 or 6 are each closed. To fill the filling area 3 with the plastic mass 7 from the capsule 8 a piston 13 which can be moved within the capsule is provided. The clamping rings 9 or 10, the opening sliders 11 or 12 and also the piston 13 are remotely operated or at least partly controlled by a person operating the catheter 2. The catheter 2 is already positioned with its filling area 3 at the position intended for the stent.

Figure 2:
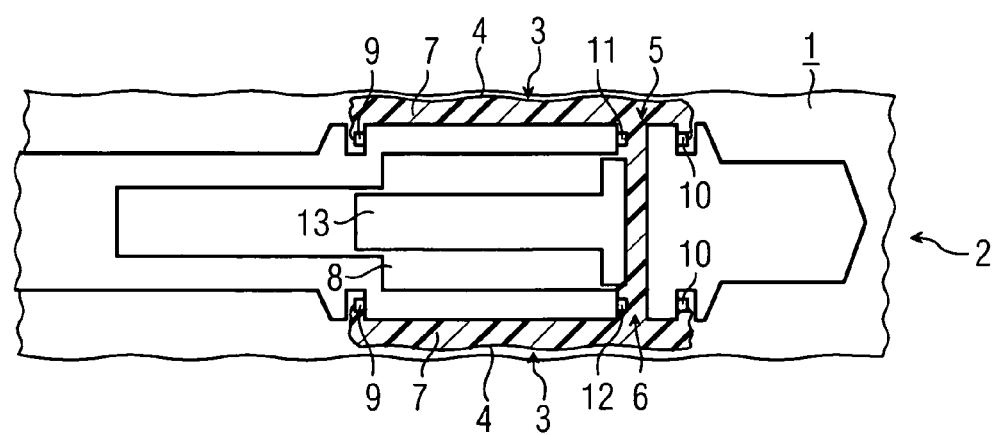
FIG. 2 the catheter shown in FIG. 1, with the filling area filled with the plastic mass and thereby expanded towards the wall of the body conduit.

FIG. 2 shows the catheter 2 from FIG. 1, with on the one hand the openings 5 and 6 being opened by moving one of the sliders 11 or 12 in each case and on the other hand the piston 13 being pushed into the capsule, so that the filling area 3 is filled with the plastic mass 7 from the capsule 8 and is thereby expanded towards the wall of the body conduit 1. This expansion does not create any undesired expansion forces since the viscous plastic mass 7 can distribute itself to adapt to the wall of the body conduit 1.

After the openings 5 or 6 have closed once more, the plastic mass 7 is hardened to produce a stent 14, depending on the plastic e.g. simply by a hardening period elapsing.

Figure 3:
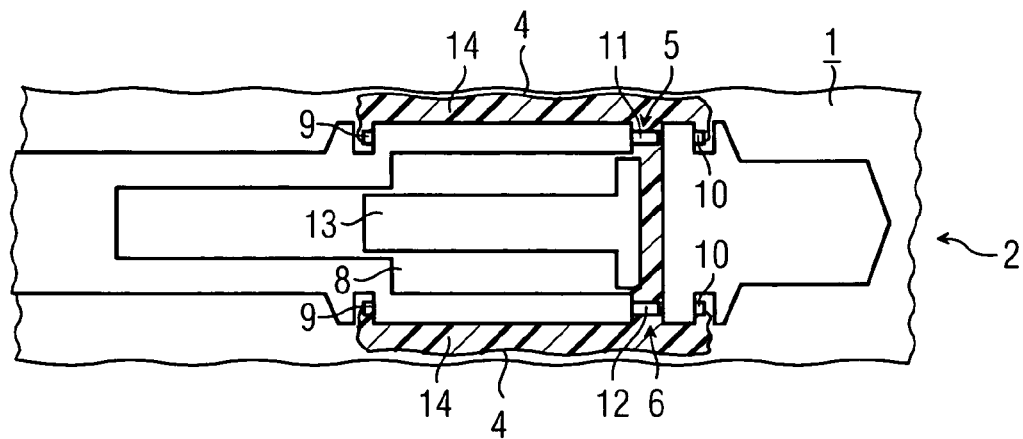
FIG. 3 the catheter shown in FIG. 2, with the openings of the capsule to the filling area closed and the envelope separated from the catheter.

FIG. 3 shows the catheter 2 from FIG. 2, with the openings 5 or 6 closed again, the plastic mass 7 already hardened into a stent 14 and in addition the envelope 5 released from the catheter 2 by retraction of the clamping rings 9 or 10. In this state it is possible to remove the catheter 2 from the body conduit 1 with the stent 14 simultaneously remaining in the body conduit 1.

To adapt the stent 14 in respect of its internal diameter, an inflatable balloon section arranged within the tubular filling area 3 is provided, which is inflated after the positioning of the filling area 3 at the position intended for the stent 14. To make the diagram as easy to understand as possible this balloon section is not included as part of the drawing in this exemplary embodiment.

Figure 4:
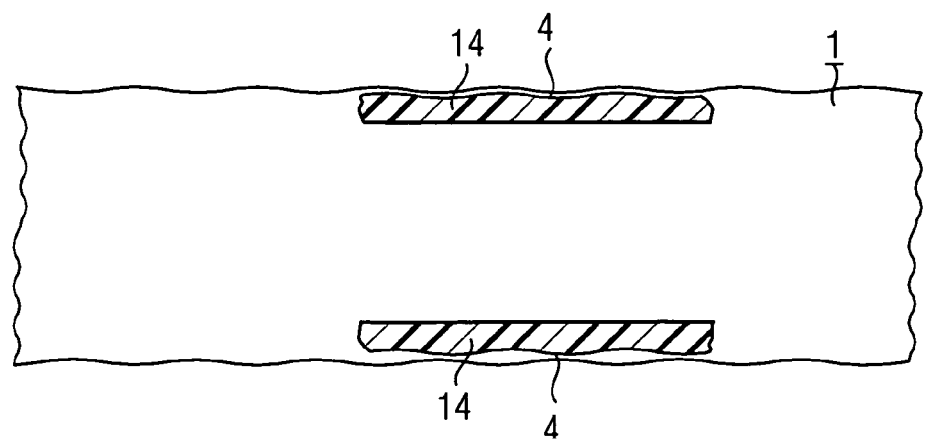
FIG. 4 the body conduit shown in FIGS. 1-3 with the stent produced by the catheter.

FIG. 4 shows the body conduit 1 from FIGS. 1-3 with the stent 14 produced by the catheter 2 after the removal of the catheter 2 from the body conduit, with the envelope 4 released from the catheter 2 remaining with it in the body conduit 1 as part of the stent 14. Mixing-in a substance impermeable to x-radiation with the plastic mass 7, enables the stent 14 produced from the plastic mass 7 to be easily recognized on an x-ray image of the body conduit 1.

To enable stents of different lengths to be produced with the same catheter, further clamping rings can be provided between the clamping rings 9 or 10. The envelope 4 is accordingly held by one of its ends with clamping ring 10 and with its other end by one of the other clamping rings.

Figure 5:
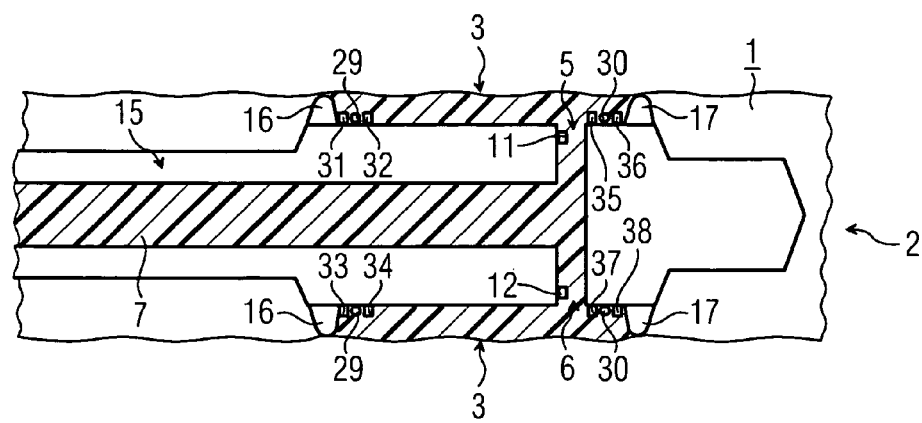
FIG. 5 in a longitudinal cross section such as that shown in FIG. 2 a catheter with a filling area, which is delimited from the rest of the body conduit by two extended sealing rings and is filled with the plastic mass via a tube arranged in the catheter.

FIG. 5 shows in a longitudinal cross section such as that shown in FIG. 2, a catheter 2 introduced into a body conduit 1 with an essentially tubular filling area 3 surrounding the catheter 2, which is delimited by two seals in the form of two elastic expansion rings 16 or 17 expanded by application of force, each of which takes in the entire circumference of the catheter 2, from the rest of the body conduit 1 and which is connected via the two openings 5 or 6 with an inner chamber arranged in the catheter 2 containing a viscous and hardenable plastic mass 7, in this exemplary embodiment in the form of a tube 15 leading to an operating end arranged outside the body conduit 1. As in the previous exemplary embodiment, in this embodiment too the two openings 5 and 6 each have an opening slider 11 or 12, with which the openings 5 or 6 can be closed in each case. In addition two markers impermeable to x-radiation in the form of two gold rings 29 and 30 are arranged around the catheter 2, which each enclose the entire circumference of the catheter 2 and are held in their position by four retaining bolts 31-34 or 35-38 arranged in pairs on opposite sides of the catheter 2 and able to be withdrawn completely into the catheter 2.

In the drawing the filling area 3 is already positioned at the position intended for the stent and is filled by introducing the plastic mass 7 via the end of the tube arranged at the operating end of the catheter 2. To simplify the filling it is useful to liquefy the plastic mass 7, e.g. by heating it beforehand. After the plastic mass 7 has hardened into the stent the next steps provided are to close the openings 5 or 6 with the opening sliders 11 or 12, to harden the part of the plastic mass located in the filling area 7 into a stent, to release the stent from the catheter 2 by retracting the rings 16 or 17 by means of a pressure reduction, to retract the retaining bolts 31-38 fully into the catheter and to remove the catheter 2 from the body conduit 1, with the stent remaining as intended in the body conduit 1.

It is also possible to retract the retaining bolts 31-34 or 35-38 before the filling of the filling area 3 or at least before the hardening-off of the plastic mass 7, if nec. coupled with the closing of the openings 5 or 6 by the opening sliders 11 or 12, in order to avoid the retaining bolts 31-34 or 35-38 pressing into the hardening plastic mass 7 and causing unevenness in the stent.

Figure 6:
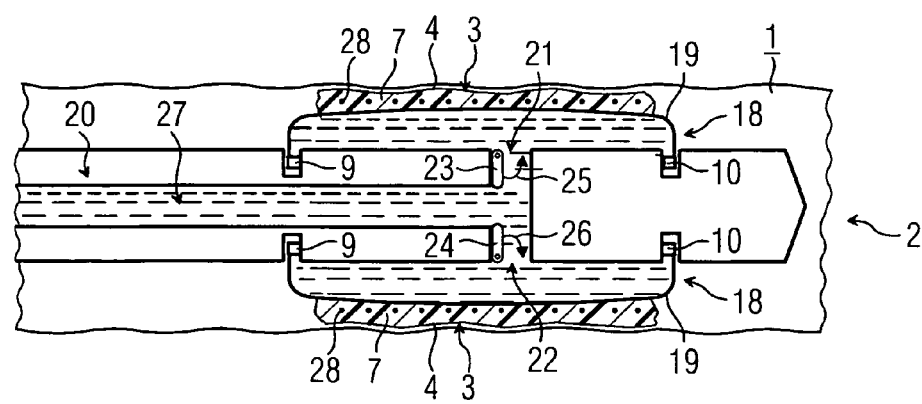
FIG. 6 in a longitudinal cross section such as that shown in FIG. 2 or FIG. 5, a catheter with an inflated balloon section and with a filling area surrounding this which is enclosed within an envelope and is filled with the plastic mass.

FIG. 6 shows, in a longitudinal cross section such as that shown in FIG. 2 or 5, a catheter 2 introduced into the body conduit 1 with a filling area 3 which is enclosed by an envelope 4 and is already filled with a plastic mass 7 on introduction of the catheter 2 into the body conduit 1. The filling area 3 is embodied so that, in addition to the plastic mass 7, it can also accommodate a wire mesh 28 encapsulated by the plastic mass 7, which is provided for additional stabilization of the stent formed later by the hardening of the plastic mass 7. Within the essentially tubular filling area 3 is arranged a balloon section 18 belonging to the catheter 2, of which the balloon envelope 19—like the envelope 4 of the filling area 3 in FIGS. 1 and 2—is held onto the catheter 2 at its front and rear end by an expandable and retractable clamping ring 9 or 10 in each case, so that the inner area of the balloon section 18 is completely closed off from the body conduit 1. The filling area 3 is completely surrounded by the envelope 4 and the balloon envelope 19 together. The balloon section 18 is connected via two line openings 21 or 22 with a line 20 arranged in the catheter 2 which leads to the operating end of the catheter 2 and to which a fluid 27, e.g. in the form of a cooking salt solution, can be fed to the balloon section 18. The line openings 21 and 22 can be closed off with the aid of a flap 23 or 24 by hinging the flaps in the direction 25 or 26.

In the drawing the filling area 3 is already positioned at the position intended for the stent and the balloon section 18 is inflated by feeding the fluid 27 into it, so that the filling area 3 is pressed with the plastic mass 4 onto the wall of the body conduit 1. The internal diameter of the stent which can be made from plastic is determined by the volume of the fluid 27 fed into the balloon section 18. After the plastic mass 7 hardens into the stent, the next steps provided are to close off the line openings 21 or 22 with the flaps 23 or 24, to release the balloon envelope 19 and thus also the envelope 4 of the filling area 3 and the stent from the catheter 2 by retracting the clamping rings 9 or 10 and finally to remove the catheter 2 from the body conduit, with the balloon envelope 19 and the envelope 3 remaining with the stent as components of it in the body conduit 1. Usefully the non-functioning free ends of the balloon envelope 19 consist of a material which can be broken down by the body, so that after a time necessary to break down the free ends, only the hardened plastic mass 4 of the stent, if necessary with an encapsulation surrounding the plastic mass, remains behind.

It is possible, for hardening the plastic mass by heating it up, to arrange a heating element in the catheter 2, e.g. in its balloon section 18. In addition the plastic mass can be heated up indirectly by a heating means arranged at the operating end of the catheter, from which the heat is transported to the plastic mass 7 via the fluid 27 circulating in the tube 15; to this end a conduit for feeding in the heated fluid 27 and a further conduit for taking away the fluid cooled by the heat dissipation to the plastic mass 7 can be provided in the tube 15.

It is further possible not to leave the balloon envelope 18—permanently connected to the catheter 2—in the body conduit 1, but to remove it together with the catheter 2 from the body conduit 1.

The invention can be summarized as follows: In order to create a stent, which despite being simple to guide in the relevant body conduit allows flexible adaptability to the body conduit while avoiding undesirably high expansion forces on the wall of the body conduit, in accordance with the invention, a catheter is provided with an essentially tubular filling area surrounding the part of the catheter which can be introduced into the body conduit, which can be filled with a plastic mass which forms the stent by a process of hardening; there is provision for positioning the filling area at the position intended for the stent in the body conduit, for hardening the plastic mass in the filling area for creating the stent and removing the catheter from the body conduit with the stent remaining in the body conduit.

The invention claimed is:

1. A catheter for forming a plastic stent at a position in a body conduit of a patient, comprising:
    an tubular filling area surrounding a part of the catheter and positionable along a selected portion of the body conduit;
    a plastic mass transferable to fill the tubular filling area and forms the stent by hardening the plastic mass in the filling area;
    an envelope completely surrounding the filling area to prevent plastic mass in the filling area from escaping into other portions of the body conduit than the selected portion, and for influencing the form of the stent; and
    an inner chamber of the catheter connected to the filling area that temporarily accommodates the plastic mass.

2. The catheter as claimed in claim 1, wherein the body conduit is a blood vessel of the patient.

3. The catheter as claimed in claim 1, wherein the inner chamber is connected to the filling area by an opening which is closed after the filling.

4. The catheter as claimed in claim 1, wherein the filling area is expandable to adapt a structure of the body conduit by filling with the plastic mass.

5. The catheter as claimed in claim 4, wherein the plastic mass is a polymer and bio-compatible.

6. The catheter as claimed in claim 5, wherein the polymer is a silicon or a rubber elastomer.

7. The catheter of claim 1 wherein the envelope is releasable from the catheter so that it remains in the body conduit as a part of the stent after the catheter is removed from the body conduit.

8. The catheter as claimed in claim 1, wherein a closable capsule is a part of the inner chamber extending over part of the catheter.

9. The catheter as claimed in claim 1, wherein a tube is a part of the inner chamber leading to an operating end of the catheter outside of the body conduit.

10. The catheter as claimed in claim 1, wherein the plastic mass is liquefied or hardened by changing a temperature of the plastic mass.

11. The catheter as claimed in claim 1, wherein an inflatable balloon section is arranged within the tubular filling area.

12. The catheter as claimed in claim 1, wherein the filling area accommodates a wire mesh which is encapsulated with the plastic mass.

13. The catheter as claimed in claim 1, wherein the filling area accommodates a marker which is encapsulated with the plastic mass and impermeable to an x-radiation.

14. The catheter as claimed in claim 1, wherein the plastic mass is mixed with a contrast medium which makes the stent visible in an image.

* * * * *